United States Patent [19]

D'Alise

[11] Patent Number: 5,468,149
[45] Date of Patent: Nov. 21, 1995

[54] DUAL FUNCTION PROSTHETIC LOCKING DEVICE FOR ENDOSSEOUS DENTAL IMPLANTS

[76] Inventor: James V. D'Alise, 120 Oad Brook Center Mall, Oak Brook, Ill. 60521

[21] Appl. No.: 232,448

[22] Filed: Apr. 21, 1994

Related U.S. Application Data

[63] Continuation of Ser. No. 944,091, Sep. 14, 1992, abandoned.

[51] Int. Cl.⁶ ........................................... A61C 8/00
[52] U.S. Cl. ............................................ 433/173; 433/174
[58] Field of Search .................................. 433/172, 173, 433/174, 175, 176

[56] References Cited

U.S. PATENT DOCUMENTS

| | | | |
|---|---|---|---|
| 4,645,453 | 2/1987 | Niznick | 433/173 |
| 4,758,161 | 7/1988 | Niznick | 433/173 |
| 4,799,886 | 1/1989 | Wimmer | 433/176 |
| 4,854,873 | 8/1989 | Linden | 433/173 |
| 4,960,381 | 10/1990 | Niznick | 433/174 |
| 5,076,788 | 12/1991 | Niznick | 433/173 |
| 5,078,607 | 1/1992 | Niznick | 433/174 |

*Primary Examiner*—Nicholas D. Lucchesi
*Attorney, Agent, or Firm*—Jefferson Perkins

[57] ABSTRACT

A dual function locking device for endosseous dental implants containing a receptacle having a plurality of circular threads and a plurality of sides suitable for use with both screw-in or threaded, and press-fit implant attachment.

1 Claim, 1 Drawing Sheet

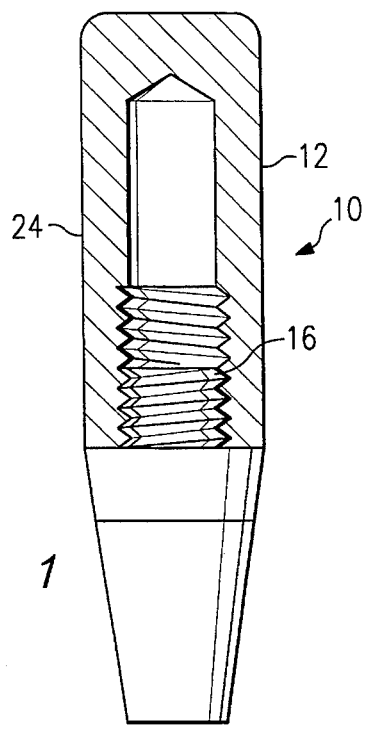
FIG. 1
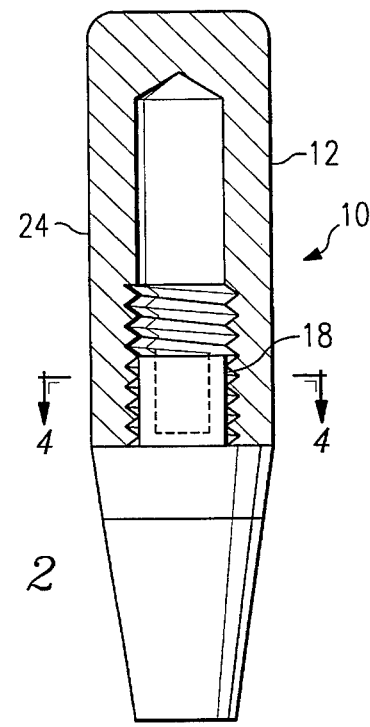
FIG. 2
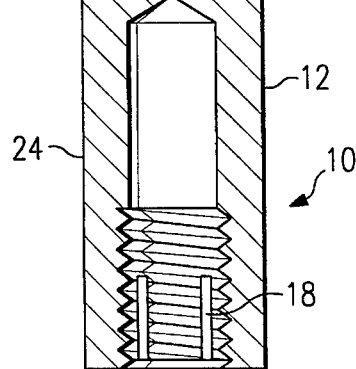
FIG. 3
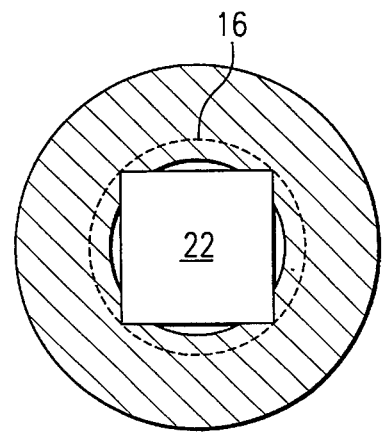
FIG. 4
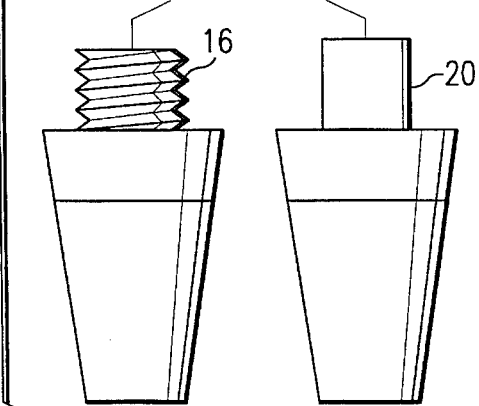

DUAL FUNCTION PROSTHETIC LOCKING DEVICE FOR ENDOSSEOUS DENTAL IMPLANTS

This application is a continuation of Ser. No. 07/944,091 filed Sep. 14, 1992 now abandoned

BACKGROUND OF THE INVENTION

1. Field of Invention

This invention is generally related to artificial root substitutes surgically placed into human jaw bones, and is specifically directed to a locking device for use in a endosseous dental implant suitable for use with both screw type and press-fit prosthetic attachments.

2. Description of Prior Art

Dentists and dental manufacturers commonly supply and use two different types of dental implants: a threaded or screw-type implant, or a press-fit implant, often custom made. Frequently, the type of implant chosen depends on the ability of the implant to maintain its position within the jaw over a period of time. Because the press fit implant typically permits growth of bony tissue within the implant, this type of implant is particularly suitable in instances where there is a potential for improper healing. On the other hand, a threaded implant head is easier to fit and generally more stable over time.

Sometimes jaw bone topography, the shape or size, will not allow for the implant to be positioned in parallel with other abutments. Inherent placement discrepancies later found will often make restoration difficult, if not impossible. A threaded or screw in type of implant is limited by its angle and alignment of the attaching head. Notwithstanding, several types of threaded designs such as floating and indirect screws have been proposed to alleviate the unforeseen alignment problems. These devices are difficult and expensive to install. Moreover, after a prosthetic head is installed, any misalignment of abutments create a higher risk of failure. On the other hand, a custom made press-fit head can be used to precisely meet the paralleling requirements. However, this type of attachment head will typically not work or fit properly in the threaded type implant previously installed. Worse yet, once an implant is integrated within the jaw bone, the edentulous jaw must be rehabilitated if a different type of head is necessitated or preferred.

Therefore, a need exists for a single implant body that can accommodate both a screw-in and press-fit type prosthetic attachments.

SUMMARY OF THE INVENTION

The present invention is a dual function prosthetic locking device for endosseous dental implants. The subject invention is illustrated in one preferred embodiment. The invention is designed to provide a more accurate prosthetic tooth replacement at a lesser cost.

The dual purpose locking device of the present invention comprises a dental endosseous implant body having a rigid metal body of varying lengths and widths, and a receptacle suitable for accommodating both a screw-in type head and press-fit type prosthetic attachments. The receptacle of the subject invention allows for both threaded/screw-in and multi-sided stemmed metal prosthetic attachments to be inserted into the same implant body, functioning as one unit. This dual purpose prosthetic locking device may be of varying lengths, widths and forms including but not limited to rectangular shape, plate forms, and trapezoidal shape.

The manner of using the dental implant body is similar to what is presently in use. The receptor site is surgically drilled into the jaw bone and is trephined to a specific depth and width. The implant body is placed into the bone and a healing cap is screwed into the implant body, with the gum tissue placed over it. The implant is then left to heal for three to five months. Once healing has taken place, the clinician surgically uncovers the dental implant body and removes the healing cap. A proper aligned attachment is then either screwed in or press fitted and cement into place.

It is an object and feature of the present invention to provide a locking device for an endosseous dental implant which will accommodate both a threaded or press fit type of prosthetic attachment head.

It is a further object and feature of the present invention to provide a locking device that does not require the dentist to pre-select two different types of dental implant bodies before surgical placement.

Another object and feature of the present invention is to provide a locking device that allows the clinician to place the implant body into the best available bone and provide the best possibility for long term success under chewing function.

Another object and feature of the present invention is to provide a locking device that allows for the clinician and laboratory technician to properly align the prosthetic heads for the accurate fabrication of tooth replacement.

Another object and feature of the present invention is to provide a locking device that does not require an implant body to be dismantled at each working appointment, therefore reducing the amount of wasted clinical time.

Another object and feature of the present invention is to provide a more accurate transfer of the laboratory work to the mouth with no errors.

These and other objects and features of the invention will be readily apparent from the accompanying drawings and detailed description of the preferred embodiments.

BRIEF DESCRIPTION OF DRAWINGS

FIG. 1 is a side elevation view of the present invention with parts broken away.

FIG. 2 is a side elevation view of the present invention with parts broken away.

FIG. 3 is an exploded view of the side elevation with parts broken away.

FIG. 4 is a cross sectional view taken along line 4—4 of FIG. 2.

DETAIL DESCRIPTION OF THE PREFERRED EMBODIMENT

The present invention is a dual purpose prosthetic locking device 10 for endosseous dental implants. The subject invention is illustrated in a single preferred embodiment.

Prior to integrating the implant body into the jaw bone, the type of implant and prosthetic tooth attachment, press fit or threaded, is selected. A receptor site is surgically drilled into the jaw bone and is trephined to a specific depth and width that will receive the implant body. The implant is then placed into the bone, covered by a healing cap and gum tissue, and allowed to heal for three to five months. After the healing has taken place, the clinician surgically uncovers the dental implant and removes the healing cap. The implant attachment or head is then attached.

The dual purpose prosthetic locking device 10 of the subject invention comprises an implant body 12 having a receptacle 14 which accommodates both a threaded or screw-in and a press fit type prosthetic attachments. The implant body 12 is placeable in the jaw bone for replacing a natural tooth root. The receptacle 14 of the implant body 12 comprises a plurality of circular screw threads 16 and a multisided lock 18. The multisided lock 18 comprises a plurality of sides suitable for accommodating a multisided stemmed attachment 20.

The implant body 12 is placed into the human jaw bone and used to replace an extracted human tooth or teeth. The implant body 12 is a rigid metal container 24 having varying length 26 and diameter 28. It may be a variety of shapes including but not limited to a rectangular shape, plate form or trapezoidal shape.

As shown in FIGS. 2, 3, and 4, the receptacle 14 of the implant body 12 of the has a multisided lock 18 with circular screw threads 16 cut into its inside diameter 30. The combination of the multisided lock 18 and screw threads 16 allow for both types of attachments, screw-in and press fit, to be placed into the same implant body.

While the preferred embodiment of the present invention has been illustrated and described, it will be understood that changes and modifications can be made without departing from the invention and its broader aspects.

I claim:

1. A dual function prosthetic locking device for an endosseous dental implant body comprising:

a dental endosseous implant body to replace a natural tooth root having a rigid metal body placeable in the jaw bone, said rigid metal body comprising a multi-sided receptacle formed from a plurality of walls with circular screw threads in its inside diameter, said circular screw threads extending substantially the entire depth of the walls;

wherein said receptacle allows for a similarly threaded metal prosthetic attachment to be screwed into the metal body joining it as a unit;

wherein said receptacle of said metal body also allows a custom fitted metal prosthetic attachment with a multi-sided stem to be inserted into the implant body locking it into place with said multi-sided receptacle of the implant body so that the implant body and custom fitted metal prosthetic attachment function as one unit.

* * * * *